(12) United States Patent
Mintz et al.

(10) Patent No.: US 9,259,276 B2
(45) Date of Patent: *Feb. 16, 2016

(54) INDICATOR FOR TOOL STATE AND COMMUNICATION IN MULTIARM TELESURGERY

(75) Inventors: David Mintz, Sunnyvale, CA (US); David Q. Larkin, Menlo Park, CA (US); Michael Lee Hanuschik, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 774 days.

This patent is subject to a terminal disclaimer.

(21) Appl. No.: 13/214,439

(22) Filed: Aug. 22, 2011

(65) Prior Publication Data

US 2012/0059390 A1    Mar. 8, 2012

Related U.S. Application Data

(62) Division of application No. 11/478,416, filed on Jun. 28, 2006, now Pat. No. 8,100,133.

(60) Provisional application No. 60/695,611, filed on Jun. 30, 2005.

(51) Int. Cl.
*A61B 19/00* (2006.01)
*B25J 9/00* (2006.01)
(Continued)

(52) U.S. Cl.
CPC ........... *A61B 19/2203* (2013.01); *B25J 9/0084* (2013.01); *B25J 9/1689* (2013.01);
(Continued)

(58) Field of Classification Search
CPC ............... A61B 19/22; A61B 19/2203; A61B 19/2211; A61B 19/2215; A61B 19/2249; A61B 2017/00234; A61B 2017/00367; A61B 2017/00477; G06F 19/3406; G06F 19/3481; Y10T 74/20305
USPC ........ 606/1, 30; 901/2, 6, 8, 9, 14–19, 30, 36, 901/46, 47; 700/2, 3, 245–250
See application file for complete search history.

(56) References Cited

U.S. PATENT DOCUMENTS

| 4,281,447 A | 8/1981 | Miller et al. |
| 4,332,066 A | 6/1982 | Hailey et al. |

(Continued)

FOREIGN PATENT DOCUMENTS

| JP | 7024750 A2 | 1/1995 |
| JP | 7194610 | 8/1995 |

(Continued)

OTHER PUBLICATIONS

Chinese Patent Application No. 200680022931.5 Office Action mailed Jul. 20, 2011, 8 pages.

(Continued)

*Primary Examiner* — Ahmed Farah

(57) ABSTRACT

Medical and/or robotic devices, systems and methods can provide an indicator associated with each manipulator assembly of a multi-arm telerobotic or telesurgical system. The exemplary indicator comprises a multi-color light emitting diode (LED) mounted to a manipulator moving an associated surgical instrument, allowing the indicator to display any of a wide variety of signals. The invention may provide an additional user interface to facilitate communications between the telesurgical system and/or members of a telesurgical team.

7 Claims, 15 Drawing Sheets

(51) Int. Cl.
 *B25J 9/16* (2006.01)
 *A61B 17/00* (2006.01)
(52) U.S. Cl.
 CPC ............ *A61B19/5212* (2013.01); *A61B 19/56* (2013.01); *A61B 2017/00477* (2013.01); *A61B 2017/00734* (2013.01); *A61B 2019/2223* (2013.01); *A61B 2019/2234* (2013.01); *A61B 2019/4836* (2013.01)

(56) References Cited

U.S. PATENT DOCUMENTS

| | | | |
|---|---|---|---|
| 4,486,928 A | 12/1984 | Tucker et al. | |
| 4,500,065 A | 2/1985 | Hennekes et al. | |
| 4,512,709 A | 4/1985 | Hennekes et al. | |
| 4,706,372 A | 11/1987 | Ferrero et al. | |
| 4,710,093 A | 12/1987 | Zimmer et al. | |
| 4,793,053 A | 12/1988 | Zuccaro et al. | |
| 4,809,747 A | 3/1989 | Choly et al. | |
| 4,830,569 A | 5/1989 | Jannborg | |
| 4,832,198 A | 5/1989 | Alikhan | |
| 4,943,939 A | 7/1990 | Hoover | |
| 4,979,949 A | 12/1990 | Matsen, III | |
| 4,996,975 A | 3/1991 | Nakamura | |
| 5,018,266 A | 5/1991 | Hutchinson et al. | |
| 5,078,140 A | 1/1992 | Kwoh | |
| 5,143,453 A | 9/1992 | Weynant nee Girones | |
| 5,154,717 A | 10/1992 | Matsen, III | |
| 5,174,300 A | 12/1992 | Bales et al. | |
| 5,217,003 A | 6/1993 | Wilk | |
| 5,221,283 A | 6/1993 | Chang | |
| 5,236,432 A | 8/1993 | Matsen, III | |
| 5,255,429 A | 10/1993 | Nishi et al. | |
| 5,257,998 A | 11/1993 | Ota et al. | |
| 5,271,384 A | 12/1993 | McEwen et al. | |
| 5,294,209 A | 3/1994 | Naka et al. | |
| 5,305,203 A | 4/1994 | Raab | |
| 5,312,212 A | 5/1994 | Naumec | |
| 5,313,935 A | 5/1994 | Kortenbach et al. | |
| 5,343,385 A | 8/1994 | Joskowicz et al. | |
| 5,354,314 A | 10/1994 | Hardy et al. | |
| 5,355,743 A | 10/1994 | Tesar | |
| 5,359,993 A | 11/1994 | Slater et al. | |
| 5,372,147 A | 12/1994 | Lathrop, Jr. et al. | |
| 5,397,323 A | 3/1995 | Taylor et al. | |
| 5,399,951 A | 3/1995 | Lavallee et al. | |
| 5,400,267 A | 3/1995 | Denen et al. | |
| 5,402,801 A | 4/1995 | Taylor | |
| 5,403,319 A | 4/1995 | Matsen, III | |
| 5,417,210 A | 5/1995 | Funda et al. | |
| 5,427,097 A | 6/1995 | Depp | |
| 5,451,368 A | 9/1995 | Jacob | |
| 5,649,956 A | 7/1997 | Jensen et al. | |
| 5,697,939 A | 12/1997 | Kubota et al. | |
| 5,762,458 A | 6/1998 | Wang et al. | |
| 5,784,542 A | 7/1998 | Ohm et al. | |
| 5,792,135 A | 8/1998 | Madhani et al. | |
| 5,800,423 A | 9/1998 | Jensen | |
| 6,071,281 A | 6/2000 | Burnside et al. | |
| 6,132,368 A | 10/2000 | Cooper | |
| 6,246,200 B1 | 6/2001 | Blumenkranz et al. | |
| 6,331,181 B1 | 12/2001 | Tierney et al. | |
| 6,522,906 B1 | 2/2003 | Salisbury, Jr. et al. | |
| 6,659,939 B2 | 12/2003 | Moll et al. | |
| 6,731,988 B1 * | 5/2004 | Green | 700/3 |
| 7,024,750 B2 | 4/2006 | Isokyto et al. | |
| 7,048,745 B2 | 5/2006 | Tierney et al. | |
| 7,107,090 B2 * | 9/2006 | Salisbury et al. | 600/427 |
| 7,525,274 B2 | 4/2009 | Kazi et al. | |
| 7,643,862 B2 | 1/2010 | Schoenefeld | |
| 7,666,191 B2 | 2/2010 | Orban, III | |
| 7,699,855 B2 | 4/2010 | Anderson et al. | |
| 7,727,244 B2 | 6/2010 | Orban, III et al. | |
| 7,763,015 B2 * | 7/2010 | Cooper et al. | 606/1 |
| 7,896,815 B2 | 3/2011 | Thrope et al. | |
| 7,955,322 B2 | 6/2011 | Devengenzo et al. | |
| 8,100,133 B2 | 1/2012 | Mintz et al. | |
| 8,182,470 B2 | 5/2012 | Devengenzo et al. | |
| 8,273,076 B2 * | 9/2012 | Devengenzo et al. | 606/1 |
| 2003/0109780 A1 | 6/2003 | Coste-Maniere et al. | |
| 2004/0267254 A1 | 12/2004 | Manzo et al. | |
| 2005/0004707 A1 | 1/2005 | Kazi et al. | |
| 2005/0200324 A1 * | 9/2005 | Guthart | A61B 19/22 318/568.11 |
| 2006/0052684 A1 | 3/2006 | Takahashi et al. | |
| 2006/0178559 A1 * | 8/2006 | Kumar et al. | 600/109 |
| 2007/0073137 A1 * | 3/2007 | Schoenefeld | 600/407 |
| 2007/0142969 A1 | 6/2007 | Devengenzo et al. | |
| 2012/0330325 A1 | 12/2012 | Devengenzo et al. | |

FOREIGN PATENT DOCUMENTS

| | | |
|---|---|---|
| JP | 2003339736 A | 12/2003 |
| JP | 2005536314 A | 12/2005 |
| WO | WO9313916 | 7/1993 |
| WO | WO9426167 | 11/1994 |
| WO | WO9516396 | 6/1995 |
| WO | WO9530964 | 11/1995 |
| WO | WO9639944 | 12/1996 |
| WO | WO-2007005555 A2 | 1/2007 |

OTHER PUBLICATIONS

Chinese Patent Application No. 200680022931.5 Office Action mailed May 10, 2010, 8 pages.
Chinese Patent Application No. 200680022931.5 Office Action mailed Oct. 25, 2010, 7 pages.
Japanese Appl. No. 2008-519585 Office Action dated Sep. 26, 2011, 7 pages, including English translation.
"PCT/US06/25465 International Search Report and Written Opinion of the International Search Authority, mailed Apr. 3, 2007, 12 pages.".
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Co-pending U.S. Appl. No. 60/752,755, filed Dec. 20, 2005.

* cited by examiner

MANIPULATOR UI-PROPOSAL

0 = Off, 1 = Red, 2 = Green, 3 = Dim Blue, 4 = Yellow, 5 = Blue, 6 = Purple, 7 = White, 8 = Dim Purple

| MODE | LED's | NOTES |
|---|---|---|
| Instrument/Camera Arm Clutch | Change to ISO 8583 for aesthetics<br>Does not infringe on UL | Any UI status associated with are is indicated by LED<br>Separates are identification and status<br>Arms: 1, 2, 3, C or colored labels = Red/Green/Yellow/White<br>Phased feel<br>Blue is dominant color for aesthetics<br>Yellow = reference monitor for problem explanation  Red = error<br>• Reinforce with fast blink rate     7 colors<br>• Reinforce with fast blink rate |
| No Sterile Adapter Present | Off | |
| Remove Instrument for Homing | Blink F Yellow/Off | |
| Sterile Adapter Engagement Delay | White | |
| Sterile Adapter Engaged/Ready for Tool Engagement | White | |
| Invalid Sterile Adapter | Blink F Yellow/Off | |
| Instrument Engagement Delay | Blink M Dim Blue/White | |
| Good Instrument<br>• Good Instrument; X lives left<br>• Instrument expires after use | Dim Blue | |

FIG. 10

| | | |
|---|---|---|
| Bad Instrument<br>• No more uses left on instrument<br>• Invalid instrument | Blink F Yellow/Off | |
| In Following | Blue | |
| Camera Control | Blue | |
| Guided Tool Change | Blink M. White - ready for GTC<br>White - not ready for GTC/sterile adapter present<br>Blink M Dim Blue/White - instrument engagement delay<br>Blink M Dim Blue/Off - searching for e-ball<br>Blink F Yellow/Off - invalid instrument | |
| Instrument/Camera Arm Clutch | If instrument installed Blink M half Off/Blue half Blue/Off<br>If no instrument installed Blink M half Off/White half White/Off | |
| Error State<br>• Arm associated fault<br>• Unable to home | Blink F Red/Off | |
| Match Grips | | |
| System on Battery | Blink M Yellow/Off All Arms | |
| Scope Angle Selection | | |

FIG. 10
*(Continued)*

| | |
|---|---|
| Inadequate Reserve Power (PSC) | Blink M Red/Off All Arms |
| Excessive Force (PSC Collision) | |
| Dual Console Control | Half Dim Purple at all times except following: Purple Other half is same as normal arm for all other behaviors Instrument/Camera Arm Clutch is same as normal |
| SUJ Clutch | N/A |
| Master Clutch | N/A |
| Coag/Cut | N/A - Cool Blue |

FIG. 10
*(Continued)*

| Color | General Meaning |
|---|---|
| OFF (BLACK) | System Off |
| RED (accompanied by text message) | Fault Condition |
| YELLOW (accompanied by text message) | Warning Condition |
| GREEN (accompanied by text message) | System OK, or System Temporarily Busy |
| BLUE | Surgeon may control PSM |
| DIM-BLUE | Surgeon controlling PSM (in following) |
| WHITE | Surgeon may not control PSM (drapes not installed, tool not installed, tool not clutched into body etc. Hence, Patient side staff needs to do something to manipulator to get it ready for surgeon control |
| PURPLE | Optionally, Remote surgeon may control PSM |
| ORANGE | Reserved for future use |

*FIG. 12*

| Indication | Specific Meaning |
|---|---|
| OFF (BLACK) | System Off |
|  | (NOTE: LEDs of Inactive PSMs will be WHITE) |
| Solid RED | Fault (system or other arm-specific, either recoverable or unrecoverable |
| Synchronous medium blinking RED | Arm-Specific Fault on this arm, (either recoverable or unrecoverable) |
| Solid YELLOW | Soft-lock Fault:<br>    System Running on Battery<br>    System Video Lost<br>    Unexpected SUJ motion |
| Syncronous slow blinking between GREEN and MED-GREEN | Instrument Data Loading |
| Solid BLUE | Surgeon may control PSM<br>- Arm Active and valid Instrument installed and clutched past cannula |
| Solid DIM-BLUE | Surgeon controlling PSM (in following) |
| Solid WHITE | Surgeon may not control PSM<br>- Arm Inactive (not selected on left-side pod)<br>- Instrument not installed or not clutched past cannula |
| Alternate Blinking WHITE | Clutching<br>- Port Clutch in progress<br>- Instrument Clutch in progress |
| Synchronous slow blinking WHITE | Guided Tool Change<br>- Pending (waiting for instrument)<br>- Searching for Eball |

INDICATOR FOR TOOL STATE AND COMMUNICATION IN MULTIARM TELESURGERY

CROSS-REFERENCES TO RELATED APPLICATIONS

This application is a divisional of U.S. application Ser. No. 11/478,416 filed Jun. 28, 2006, which claims priority to U.S. provisional application Ser. No. 60/695,611 filed Jun. 30, 2005, each of which is incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is generally related to medical and/or robotic devices, systems, and methods. In an exemplary embodiment, the invention provides an indicator associated with one or more robotic manipulator assemblies for communication of a state of the manipulator assembly or other component of the robotic system, for identification of one or more particular manipulators, or the like. The indicator(s) can provide an additional user interface between the robotic system and, for example, a surgical assistant, system operator, or the like.

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, may be reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

The servomechanism used for telesurgery will often accept input from two master controllers (one for each of the surgeon's hands) and may include two or more robotic arms or manipulators on each of which a surgical instrument is mounted. Operative communication between master controllers and associated robotic arm and instrument assemblies is typically achieved through a control system. The control system typically includes at least one processor which relays input commands from the master controllers to the associated robotic arm and instrument assemblies and back from the instrument and arm assemblies to the associated master controllers in the case of, e.g., force feedback or the like. One example of a robotic surgical system is the DA VINCI® system available from Intuitive Surgical, Inc. of Mountain View, Calif.

The roles and interaction among the persons making up a telesurgical team may differ from those of conventional surgery. As telesurgery is often performed in an internal surgical site, at least some of those working under the direction of the lead surgeon (or other robotic system operator) may not have direct access to or direct visualization of the ongoing tissue manipulations. For example, surgical assistants within the operating room may remove a first surgical instrument (such as an electrosurgical scalpel) from a manipulator and replace it with a different surgical instrument (such as a needle holder), as a surgeon may desire the use of different surgical instruments during different phases of a surgical procedure. Similarly, the assistant may reposition a surgical instrument during a procedure, so that rather than approaching the procedure from a first minimally invasive access site, the instrument is advanced toward the internal surgical site from a second, different access site. More complex robotic systems (and team interactions) may also be used. For example, as surgery is often performed with more than two tools, input devices may be provided for one or more additional surgeons, with each additional surgeon robotically controlling (for example) at least one surgical instrument.

While the new telesurgical systems, devices and methods have proven highly effective and advantageous, still further improvements would be desirable. In general, it would be desirable to provide improved robotic and/or surgical devices, systems and methods, particularly for performing telesurgical procedures. It may also be desirable to provide improved techniques for communication among the members of a telesurgical team, and for interfacing with the telesurgical apparatus so as to more fully take advantage of the capabilities of telesurgery to provide enhanced patient outcomes with improved efficiencies. It may be particularly beneficial to avoid unnecessary interruptions and distractions of a surgeon or other system operator, and to avoid delays and/or mistakes in the coordinated activities of a telesurgical team.

BRIEF SUMMARY OF THE INVENTION

The present invention is generally related to medical and/or robotic devices, systems and methods. An exemplary embodiment of the present invention provides a visual indicator associated with each manipulator assembly (and, hence, each surgical instrument) of a multi-arm telesurgical system. The exemplary indicator comprises a multi-color light emitting diode (LED), allowing the indicator to display any of a wide variety of signals through combinations of color, blinking, and the like. By establishing and using an appropriate indicator signal lexicography, the indicator can identify, for example:

whether the manipulator and surgical instrument are following input movement commands of a lead surgeon;

whether movement of the surgical instrument is inhibited (for example, when the manipulator is in a clutch mode to allow manual movement);

whether the surgical instrument is at, near, or beyond its intended useful life;

whether a second surgeon has control of the surgical instrument;

whether a fault is preventing robotic movement of the surgical instrument; and/or the like.

A surgeon may also optionally initiate a signal from one or more of the indicators so as to identify an associated surgical instrument to be removed and replaced, or the like. As the surgeon will often remain immersed in the ongoing surgical procedure, and as it may be difficult to determine which instrument was, for example, previously being controlled by the surgeon's right hand and is now to be replaced, such indicators may significantly facilitate communications between the telesurgical system and/or members of a telesurgical team, potentially increasing efficiencies and enhancing patient outcomes. An identifiable signal is output from the selected indicator to a person near by.

In a first aspect, the invention provides a robotic method comprising moving a first end effector of a first manipulator assembly in response to a first robotic command. The first manipulator assembly has a first indicator. A second end effector of a second manipulator assembly is moved in response to a second robotic command. The second manipulator assembly has a second indicator. A command is transmitted from a processor, with the command being selectably directed to the first indicator and/or the second indicator.

In many embodiments, the end effectors will include the working ends of surgical instruments. The person receiving the identifiable signal will often be a member of a robotic surgical team within an operating room, with the processor acting as a master/slave telesurgical controller. In such embodiments, a movement command may be input by a system operator, and the system operator may also select which of the manipulator assemblies is to output the first signal. This can allow the system operator to maintain his or her concentration on movements of the end effectors shown in a display while communicating to, for example, an assistant regarding a specific surgical instrument. For example, rather than telling the assistant to "replace the electrosurgical scalpel on the arm now wiggling back and forth with a needle driver," the surgeon can instead merely request a needle driver and activate the indicator of the appropriate manipulator assembly. Optionally, the processor may select the appropriate indicator and manipulator assembly, such as when the tool mounted on a manipulator reaches or exceeds its intended useful life.

The indicator will often include a visual indicator, with the first signal including a visual pattern such as blinking or the like, an identifiable color, or some other identifiable visual signal. In an exemplary telesurgical system, the indicators each include a plurality of light emitting diodes (LED). A variety of alternative indicators might also be employed, including any of the wide variety of light sources capable of generating different colors, audible indicators for generating tones or verbal signals, and the like. Preferably, a plurality of separately identifiable signals can be output from each indicator, thereby providing a user interface for communication to the assistant or the like regarding an associated manipulator assembly.

Typically, each manipulator assembly will include a manipulator movably supporting a tool holder, and a tool releasably mounted to the tool holder. The tool will generally include the end effector. The first identifiable signal may indicate, for example, a state of the tool, which specific manipulator assembly is operatively associated with a specific input device, an overall condition or state of all of the manipulator assemblies, an identity of one or more components of the selected manipulator assembly, or the like. Some listing or lexicography explaining the meaning of each identifiable signal will often be provided or known by the person receiving the signal, and that person will often take action in response to the signal, such as reconfiguring the manipulator assembly from which the signal is being output. The reconfiguration may include replacement of a tool of the manipulator assembly with another tool having a different (or the same) end effector, changing a mode of the manipulator assembly so as to initiate or inhibit master/slave movement of the end effector, or the like.

It will often be beneficial to include readily identifiable signal types or groups. For example, when the first signal includes a yellow color, it may communicate a warning that the associated manipulator assembly remains functional, but needs attention now or in the near future. A signal including a red color may communicate a sufficient fault along the robotic system chain to interrupt end effector movement.

A variety of refinements may be implemented with use of the manipulator assembly indicator. For example, the system operator who is inputting movement commands may benefit from graphical indicia in his or her display that corresponds to the first identifiable signal. Hence, when the system indicates that a tool is near the end of its life or the like by flashing the indicator, the same information may be communicated to the system operator by simple flashing of an icon on the operator's display screen, by superimposing a flashing color on the end effector of the instrument as shown in the display, or the like. In some embodiments, along with indicating which currently mounted tool or end effector is to be replaced, the processor may also energize another indicator associated with the new tool that is now desired, such as by flashing an LED at an appropriate location on a tool tray, or the like.

In another aspect, the invention provides a surgical robotic method comprising inputting a robotic movement command from a system operator to an input device. A surgical end effector of a manipulator assembly moves in response to the robotic command. The system operator views the movements of the end effector in a display while inputting the command. An identifiable visual signal is transmitted from a visual indicator of the manipulator assembly to a person nearby. In response, the person manually reconfigures the manipulator assembly.

In yet another aspect, the invention provides a surgical robotic system comprising a first manipulator assembly having a first indicator and a first end effector. The first end effector is movable in response to a first movement command. The second manipulator assembly has a second indicator and a second end effector. The second end effector is movable in response to a second movement command. A processor is coupled to the first and second indicators, and selectively induces at least one of the indicators to output a first signal identifiable by a person nearby.

BRIEF DESCRIPTION OF THE DRAWINGS

FIG. 10 is a listing of separately identifiable visual signals which may be then generated by the indicator of FIG. 6, along with their associated meanings.

FIG. 12 is a listing of indicator signal colors and associated general meanings.

FIG. 13 is a listing of indicator signals and associated specific meanings.

DETAILED DESCRIPTION OF THE INVENTION

The present invention generally provides improved robotic and/or medical devices, systems and methods. Embodiments of the present invention are particularly well suited for telesurgery, often providing an additional form of user interface that can enhance communication between a surgical system operator, an assistant, any other members of a telesurgical team and/or the telesurgical system. Other embodiments of the invention may be well suited for use in other telerobotic or robotic environments, particularly with robotic systems having a plurality of manipulators.

Figure 1:
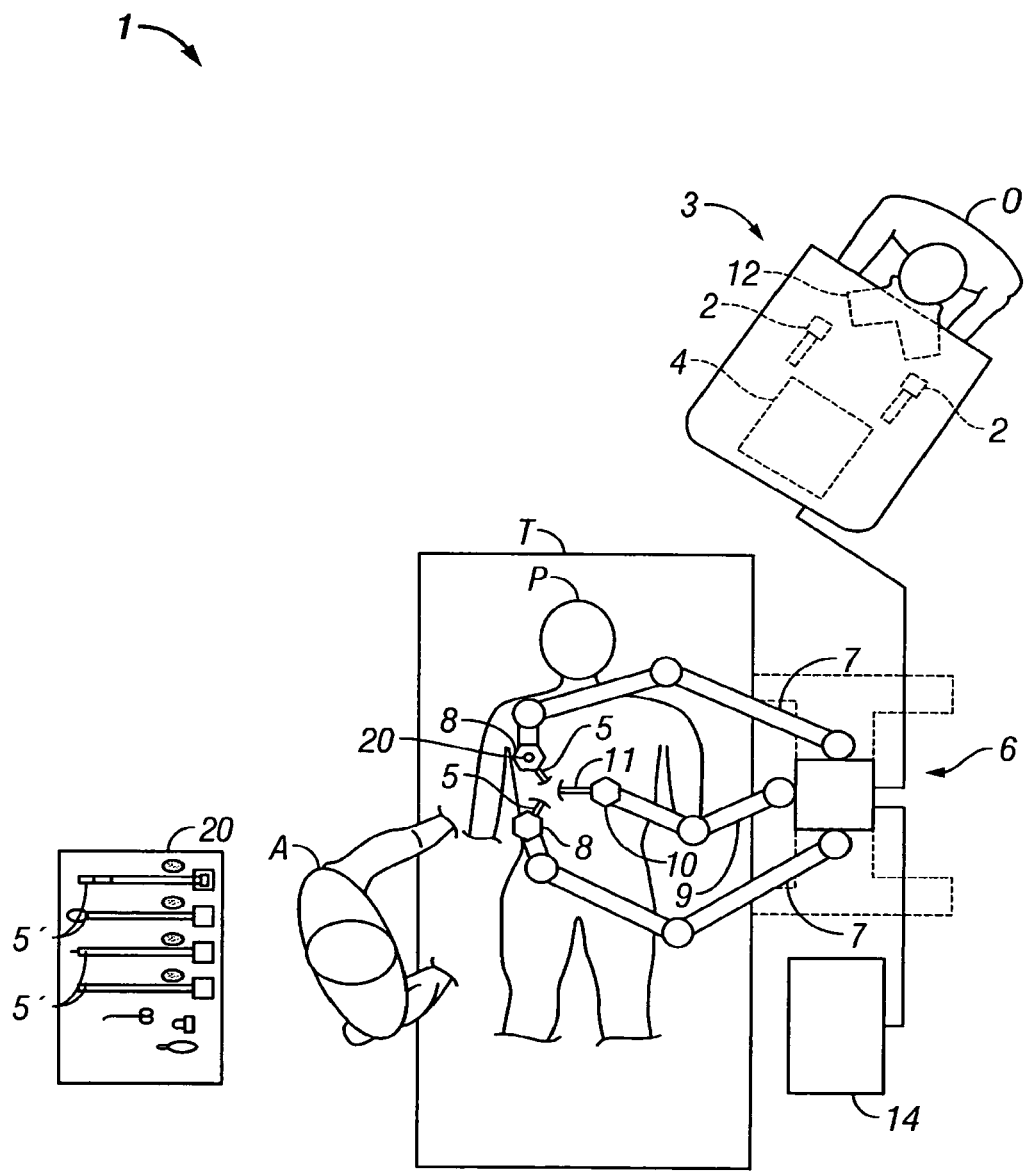
FIG. 1 is a schematic plan view of a portion of an operating theater illustrating a robotic surgical system in use, including a master surgeon console or workstation for inputting a surgical procedure and a robotic manipulator system for robotically moving surgical instruments having surgical end effectors at a surgical site within a patient.
Figure 2:
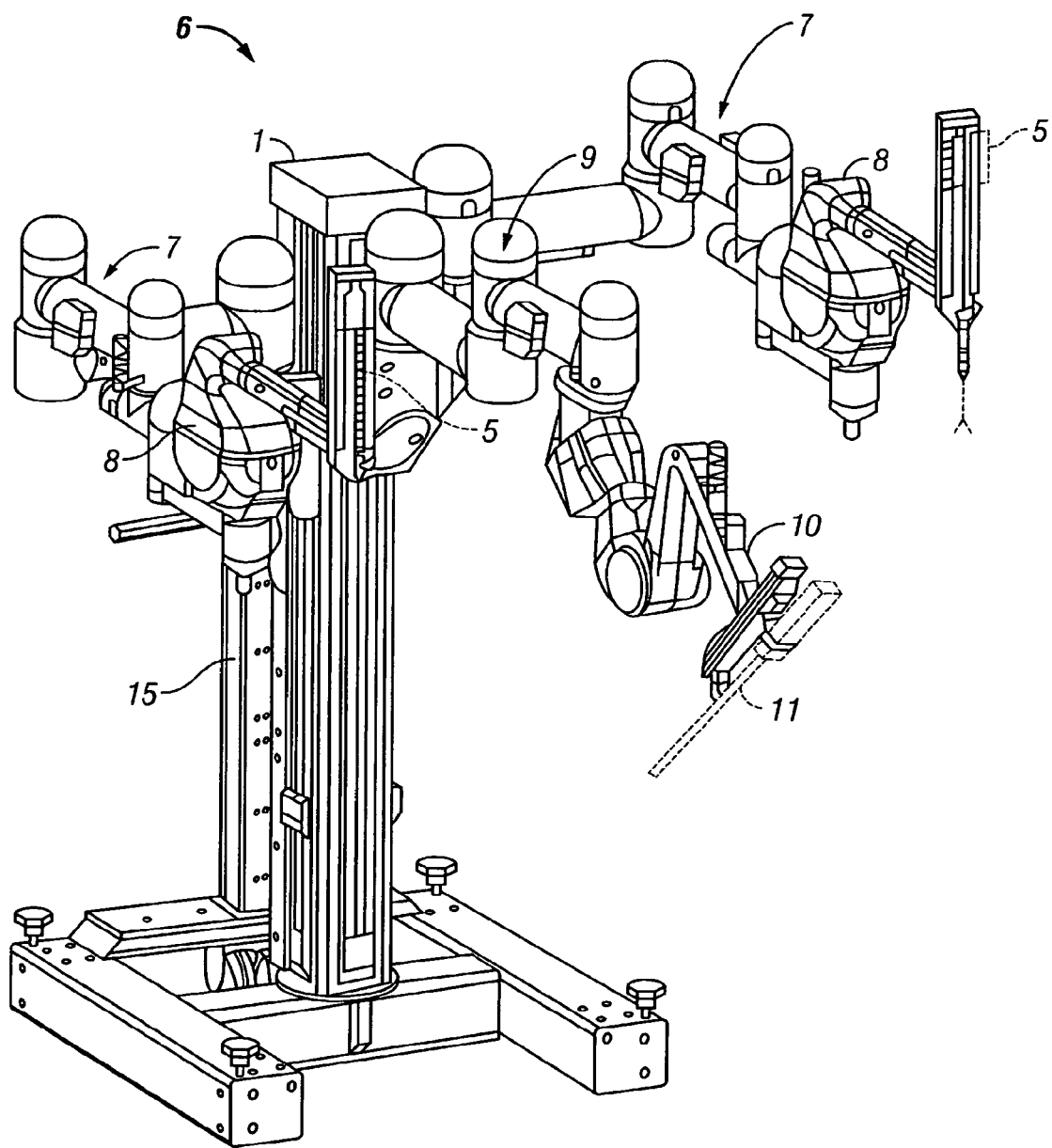
FIG. 2 is a perspective view of an exemplary manipulator system, including positioning linkages or set up joints which allow two patient side robotic manipulators and one endoscope or camera robotic manipulator to be pre-configured for surgery.
Figure 3:
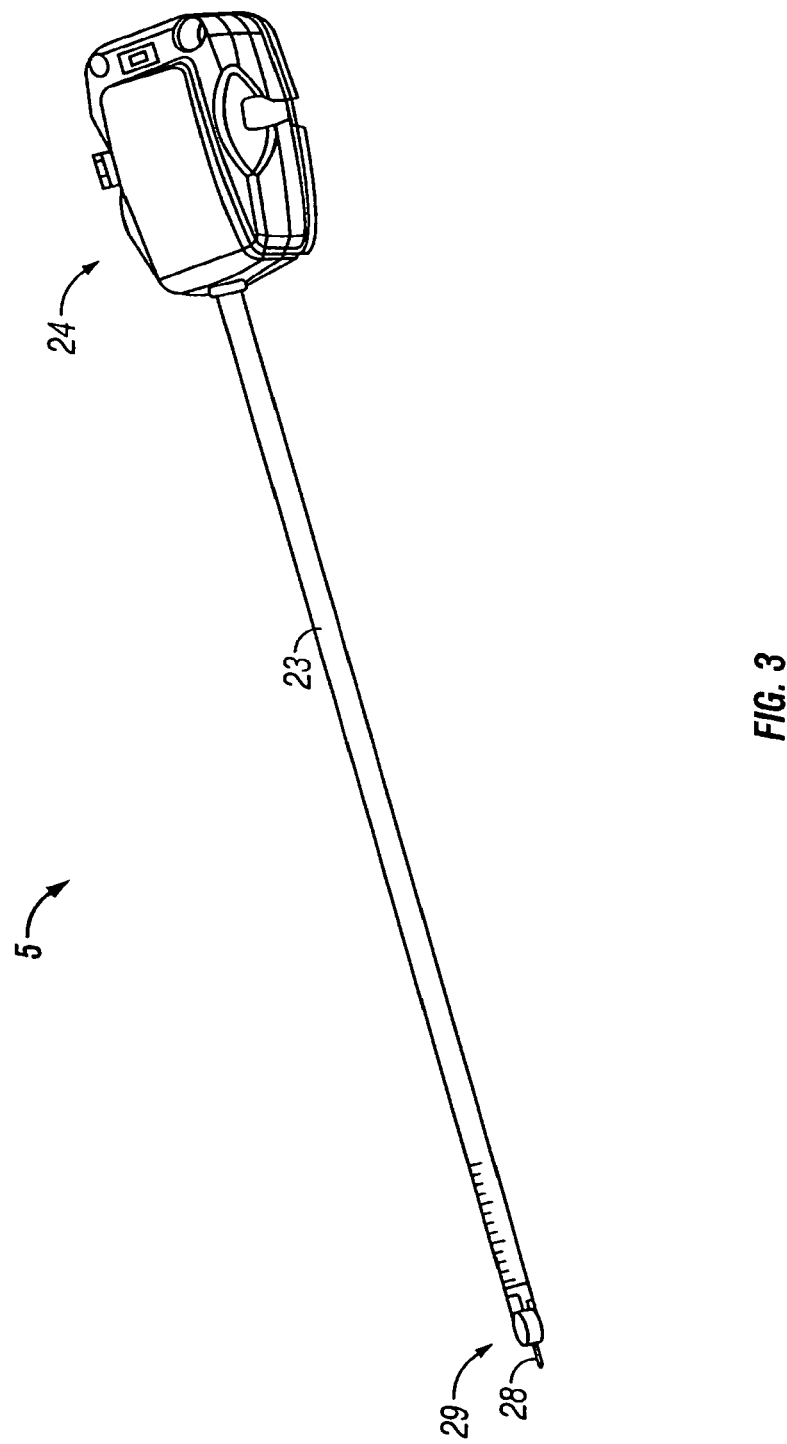
FIG. 3 is a perspective view of an exemplary articulated surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclose of which is incorporated herein by reference. A system operator O (generally a surgeon) performs a minimally invasive surgical procedure on a patient P lying on an operating table T. The system operator O manipulates one or more input devices or masters 2 at a surgeon's console 3. In response to the surgeon's input commands, a computer processor 4 of console 3 directs movement of endoscopic surgical instruments or tools 5, effecting servomechanical movement of the instruments via a robotic patient-side manipulator system 6 (a cart-mounted system in this example).

Typically, manipulator system 6 includes at least 3 robotic manipulator assemblies. Two linkages 7 (mounted at the sides of the cart in this example) support and position manipulators 8 with linkages 7 in generally supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm."

The image of the internal surgical site is shown to operator O by a stereoscopic display 12 in surgeon's console 3. The internal surgical site is simultaneously shown to assistant A by an assistance display 14. Assistant A can help prior to and during a surgical procedure. Prior to surgery, assistant A typically covers at least a portion of the system with sterile drapes. Such draping of the system may include attaching sterile adapters, cannulas, and/or the like to manipulators 8, switching one or more of the manipulators into and out of a manually articulatable clutch mode, and the like. Assistant A also assists in prepositioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like. Some or all of these activities may be facilitated by providing feedback to assistant A via the indicators described herein, with the indicators often providing feedback to the assistant regarding a state of the manipulator assembly, a state of the tool mounted thereon, and/or a state of the robotic surgical system.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A. Each associated combination of a set-up joint, manipulator and tool is encompassed within the term "manipulator assembly" as that term is used herein, although some manipulator assemblies may not include set-up joints, and the manipulator assembly will not include a tool at all times.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments, tools, image capture devices and the like which are useful for surgery.

As can be seen in FIGS. 1 and 2, indicators 20 are disposed on each manipulator assembly. In the exemplary embodiments, indicators 20 are disposed on manipulators 8, 10 near the interface between the manipulators and their mounted tools 5. In alternative embodiments, indicators 20 and may instead be disposed on set-up joints 7, 9, on tools 5, elsewhere on manipulators 8, 10, or the like, with the indicators preferably being sufficiently close to the tools so that a signal generated by a particular indicator can be readily associated with a particular tool when the signal is viewed by assistant A. In FIG. 1, additional indicators 20 are shown in a rack or other structure supporting additional tools 5', with each indicator again being associated with a particular tool (or type of tool).

As can be seen in FIG. 1, the system operator O is largely immersed in the environment of and interaction with workstation 3. The system operator sees images presented by display 12 and manipulates input devices 2, and in the exemplary embodiment, processor 4 correlates the movement of the end effectors of tools 5 so that the images of the end effectors follow the movements of the input devices in the hands of the system operator O.

It can be advantageous to avoid distracting system operator O during a surgical procedure so as to require the operator to shift his or her attention away from the internal surgical site. Even when assistant A is replacing a tool 5 with an alternative tool 5', the system operator may continue manipulating tissues with another tool, or may want to continue to view the surgical site to monitor bleeding, and/or the like. Nonetheless, it may be difficult for the system operator to communicate clearly with assistant A regarding which tool 5 is to be replaced by an alternate tool. Specifically, as endoscope 11 may be at any convenient orientation, the tool associated with the right hand of system operator O will often not be disposed to the right of the endoscope, particularly as viewed by the assistant.

So as to unambiguously identify a tool 5 to be replaced assistant A, system operator O may input a command into workstation 3 (such as by pushing a button on the input device 2, actuating foot peddle, inputting a voice command, or the like) so that indicator 20 on the manipulator assembly associated with the specific tool 5 generates a visually identifiable signal that can be viewed by the assistant. A corresponding graphical indication of the signal may be provided to system operator O in display 12, such as presentation of an appropriate icon, superimposing of text on the surgical site, the use of image processing to superimpose false colors on the image of the appropriate end effector, or the like. In response to the signal on indicator 20, assistant A can remove and replace the identified tool 5. Optionally, each alternative tool 5' may also have an associated indicator 20, allowing the processor to transmit a signal so as to indicate which alternative tool the system operator O is to be mounted on the robotic system.

There are a number of additional uses for indicators 20 in telesurgical system 1. For example, assistant A will often manually position tools 5 and endoscope 11 when setting up for a surgical procedure, when reconfiguring the manipulator system 6 for a different phase of a surgical procedure, when removing and replacing a tool with an alternate tool 5', and the like. During such manual reconfiguring of the manipulator assembly by assistant A, the manipulator assembly may be placed in a different mode than is used during master/slave telesurgery, with the manually repositionable mode as sometimes being referred to as a clutch mode. The manipulator assembly may change between the tissue manipulation mode and the clutch mode in response to an input such as pushing a button on manipulator 8 (or some other component to the manipulator assembly) thereby allowing assistant A to change the manipulator mode. By generating appropriate visually identifiable signals with indicators 20 whenever the manipulator is in clutch mode, assistant A can avoid errors and increase the efficiency of the surgical procedure.

Indicators 20 may also show an associated identifiable signal when, for example, no tool is attached to the manipulator, when a sterile adaptor or interface between tool 5 and manipulator 8 is not properly attached, if an instrument mounted onto a manipulator is incompatible with that manipulator, if the instrument has reached the end of its useful life, and/or the like. For some of these signals, system operator O may initiate generation of the signal and may specify the associated manipulator assembly from which the signal is to be produced. In others, processor 4 may initiate the signal and/or indicate which manipulator assembly(s) are to be indicated. For example, in the case of a power failure, robotic system 1 may continue to operate using backup batteries. So as to indicate to the assistant A that a power failure has occurred, indicators 20 on all manipulators may blink, optionally blinking with a yellow light as a warning. As the power in the battery is drained so that robotic system 1 can no longer continue to provide robotic movement of the tools, all indicators 20 may blink red, thereby indicating a system fault. A wide variety of alternative signals may also be provided, some of which are indicated by the exemplary lexicographies of FIGS. 10-14.

Figure 4:
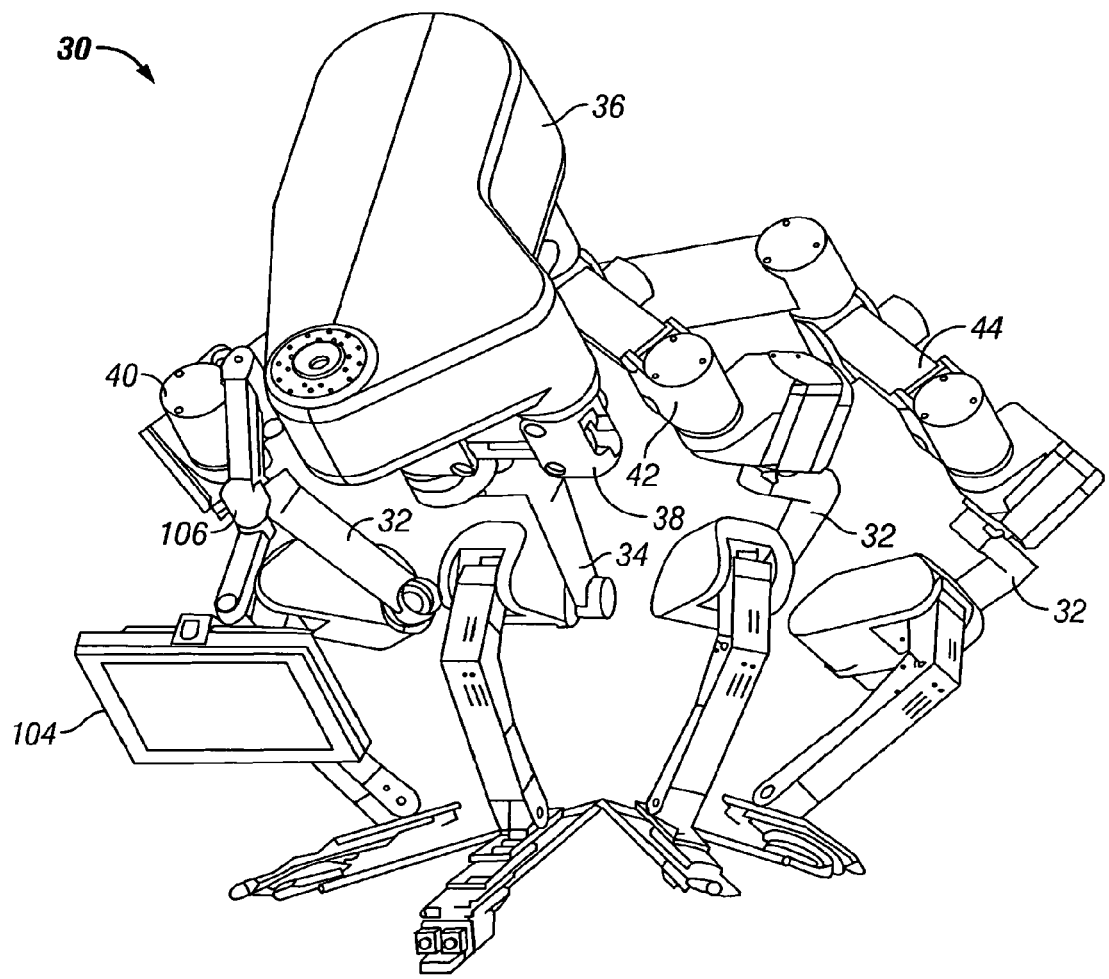
FIG. 4 is a perspective from above of an alternative manipulator system including a plurality of positioning linkages, each supporting a manipulator assembly.

FIG. 4 illustrates a perspective view of the articulated surgical tool or instrument 5. Tool 5 has a proximal housing 24 which interfaces with a tool holder of the manipulator, generally providing a quick release mounting engagement through a sterile adapter or interface. Tool 5 includes an elongate shaft 23 supporting an end effector 28 relative to proximal housing 24. Proximal housing 24 includes a drive mechanism that accepts and transmits drive signals or drive motion between the manipulator 8 and the end effector 28. Proximal housing 24 also contains circuitry that can generate signals for transmission to processor 4 so as to identify a type of the tool, indicate a remaining useful life of the tool, and/or the like. The exemplary circuitry may include a memory, such as a Dallas™ part or the like, and exemplary structures and methods for transmitting of information between the memory of tool 5 and processor 4 may be described in application Ser. No. 10/839,727, filed on May 4, 2004 and entitled "Tool Memory-Based Software Upgrades for Robotic Surgery" the full disclosure of which is incorporated herein by reference. An articulated wrist 29 may provide two degrees of freedom of motion between end effector 28 and shaft 23, and the shaft may be rotatable relative to proximal housing 24 about the axis of the shaft so as to provide the end effector 28 with the three orientational degrees of freedom within the patient's body. Control over actuation of end effector 28, such as opening or closing of jaws or the like, may represent an additional degree of freedom, for a total of four distal degrees of freedom. In some embodiments, an indicator 20 may be mounted on housing 24.

Referring now to FIG. 4, a perspective view from above of an alternative modular manipulator support assembly 30 may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 coupleable to the orienting platform. Each arm movably supports an associated manipulator 32, 34, which in turn movably supports an associated tool or an image capture device. Orienting platform 36 also supports an assistant display 104, which may be used for set-up, instrument changes, viewing of the procedure and the like. The structures and use of any of the components of modular manipulator support assembly 30 are analogous to those described above regarding manipulator system 6, and are more fully and described in copending U.S. patent application Ser. No. 11/043,688, filed on Jan. 24, 2005, and entitled "Modulator Manipulator Support For Robotic Surgery", the full disclosure of which is incorporated herein by reference. As generally described above, each manipulator 32, 34 of modular manipulator support 30 may include an indicator 20.

Figure 5:
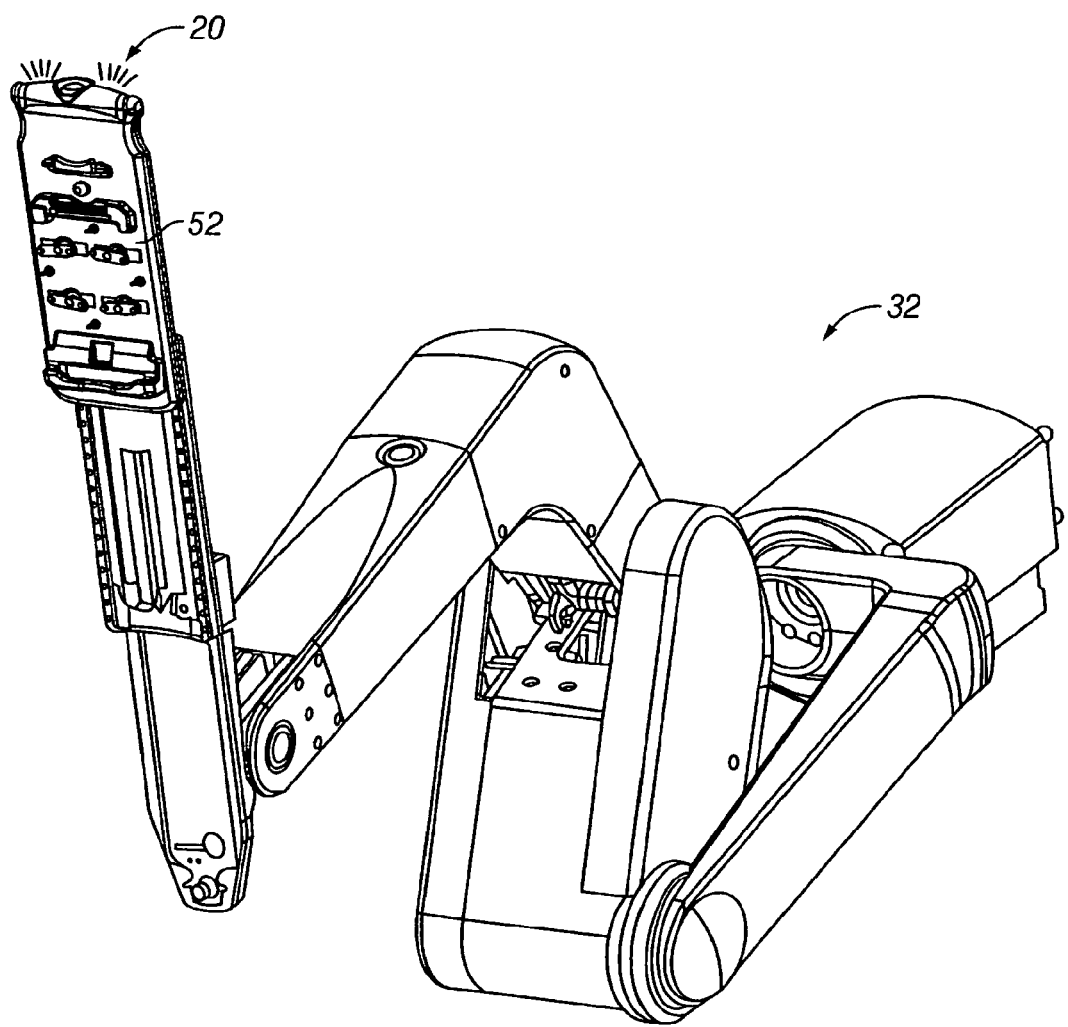
FIG. 5 is a perspective view of an exemplary manipulator for use in the manipulator system of FIG. 4.
Figure 6:
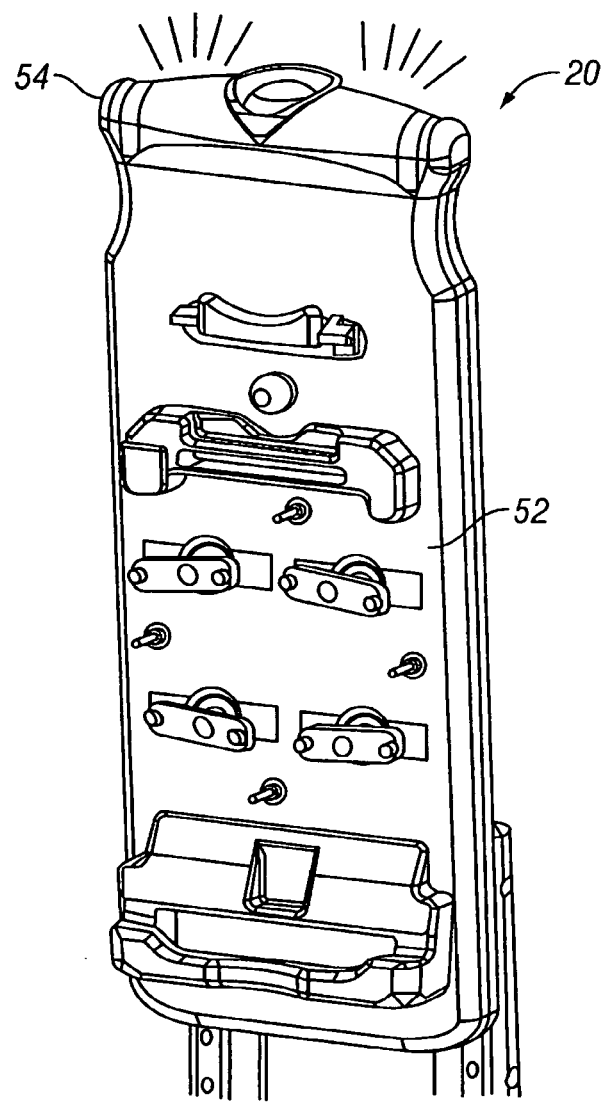
FIG. 6 is a detailed view of a portion of the manipulator of FIG. 5, showing a tool holder and adjacent indicator for outputting visual signals.
Figure 7:
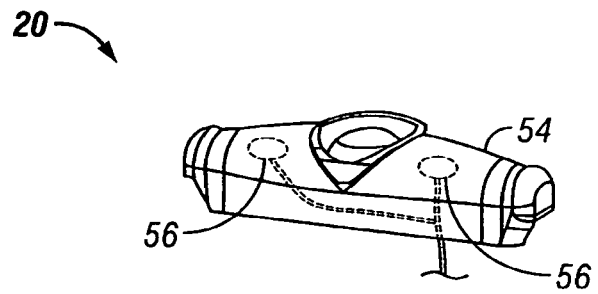
FIG. 7 shows the indicator of FIG. 6 in isolation.
Figure 11:
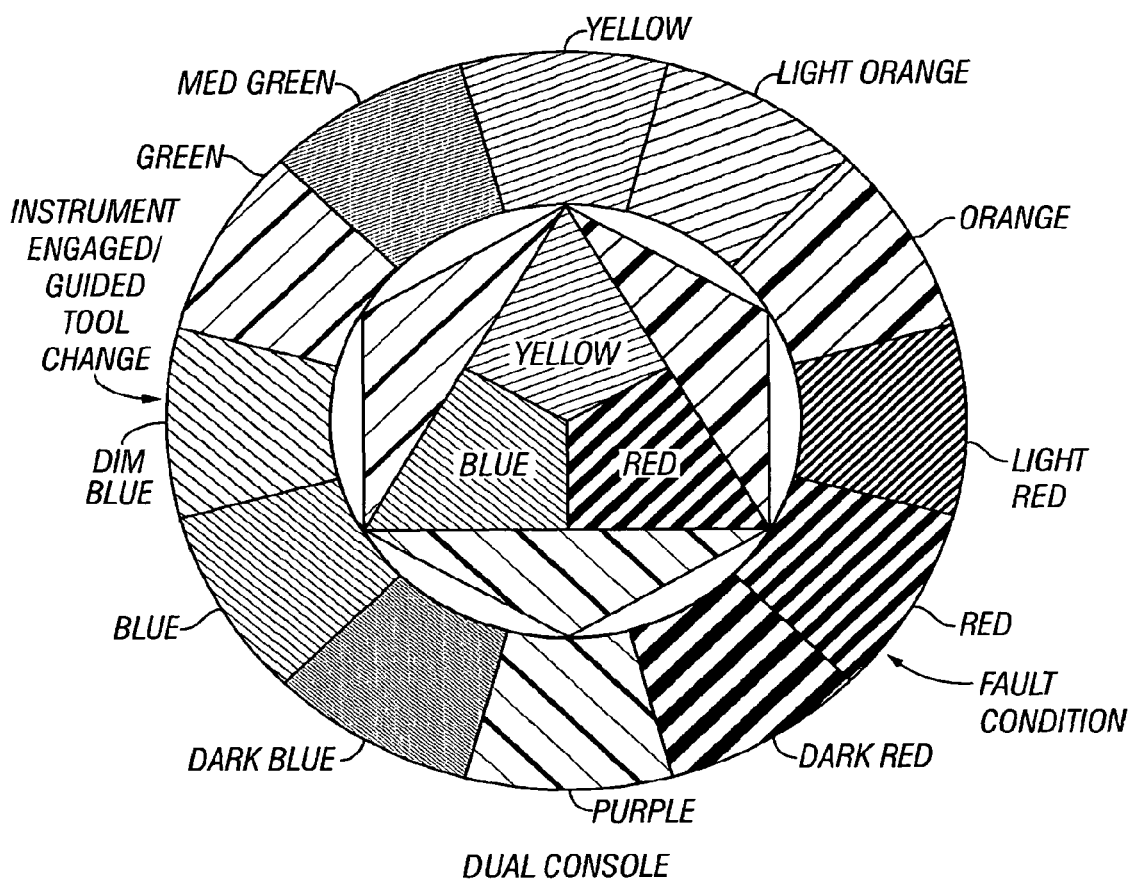
FIG. 11 illustrates colors which can be generated by the indicator of FIG. 6, along with the general meanings of those colors.
Figure 14:
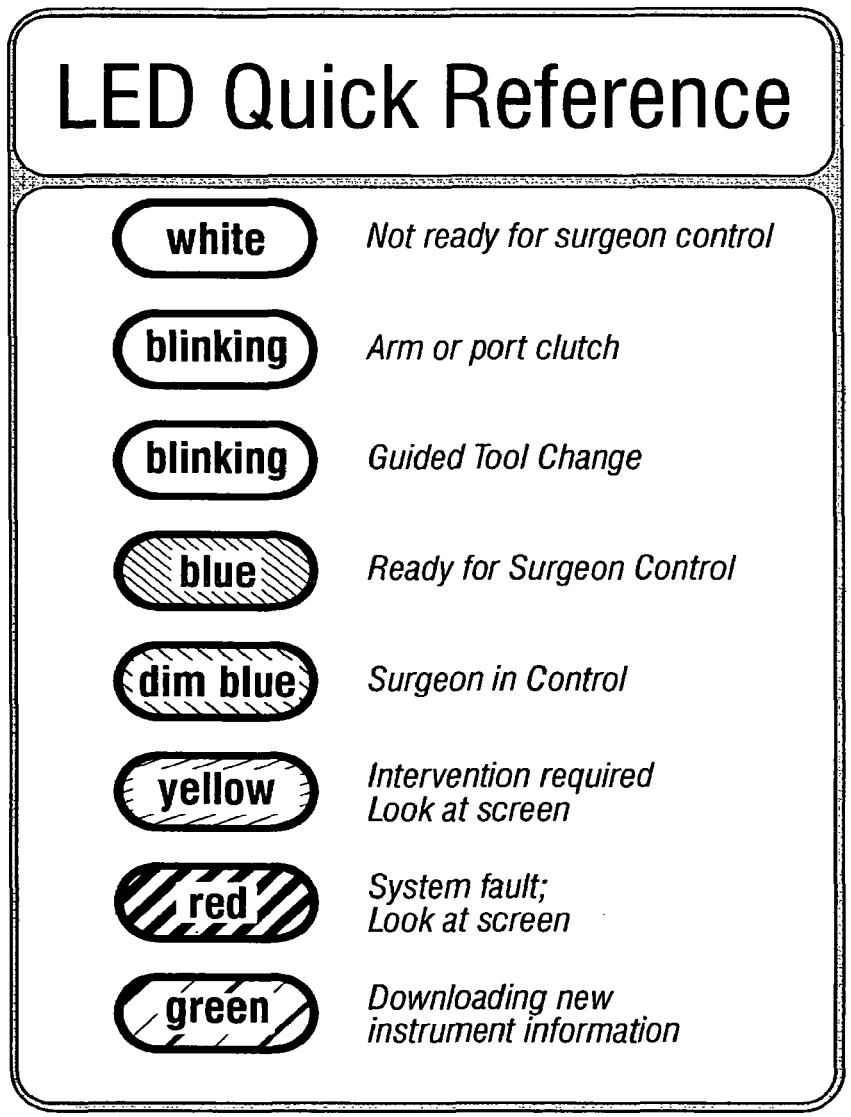
FIG. 14 illustrates An exemplary quick reference guide to the meanings of indicator signals for a telesurgical system.

Manipulator 32 is shown in more detail in FIG. 5, which also shows indicator 20 near a tool holder 52. The exemplary indicator 20 is shown in more detail in FIG. 6, and in isolation (with some of the internal components being schematically shown by dashed lines) in FIG. 7. The exemplary indicator 20 generally comprises a clear and/or translucent polymer body 54 in which a pair of light emitting diode arrays (LED) 56 are mounted. LED 56 include a red LED, a blue LED and a green LED. The LEDs of each array can be independently energized to any of a plurality of illumination or brightness levels, allowing indicator 20 to generate signals in a wide variety of colors, as schematically illustrated in FIG. 11. Additionally, the overall level of illumination from indicator 20 may be varied, and a pattern may be imposed on the cover signal by blinking and the illumination on and off, alternating between two different colors, alternating between two different illumination levels, simultaneously displaying two different colors, or the like. The speed of blinking may also be controlled or altered in more complex modulation patterns (with long and short blinks, Morse code, and the like).

As different colors may be combined with different illumination levels and different modulation patterns in a signal, a very large number of independently identifiable signals can be generated, often being more than three separately identifiable signals, typically being more than 10 separately identifiable signals, and optionally of being more than 100 separately identifiable signals. Interpretation of the identifiable signals may be facilitated by a listing correlating signals and their meaning, such as that included as FIG. 10. In some embodiments, a relatively simple signal scheme with a more limited number of signals output by indicator 20 may be combined with supplemental text or graphics output from the assistant display 114 or the like. Hence, the assistant may know that they should look for additional information on the assistant display in response to one or more signals.

So as to facilitate interpretation of the signals generated by indicators 20, any of a wide variety of signal conventions may be established and/or employed. For example, as can be understood with reference to FIG. 11, signals including the color yellow may generally indicate a warning. Optionally, the manipulator assembly may continue to function while its indicator 20 displays such a yellow warning signal, but the assistant may understand that some action may be advisable. The specific action or meaning of the warning signal may depend on other aspects of the signal, such as other colors being interspersed with a blinking yellow illumination pattern, speed of blinking, or the like. Signals including red may indicate a current or imminent fault that is now or may soon interfere with operation of the manipulator assembly. Green may optionally indicate normal operation is underway, blue may indicate an instrument or a tool is engaged, and/or that a guided tool change is underway or has been requested. Purple may indicate that a second surgeon or system operator is actively controlling the manipulator assembly, or the like. Slow blinking lights may generally indicate a less urgent state than a rapidly blinking indicator 20. Some of these possible conventions are graphically illustrated in FIG. 11.

Figure 8:
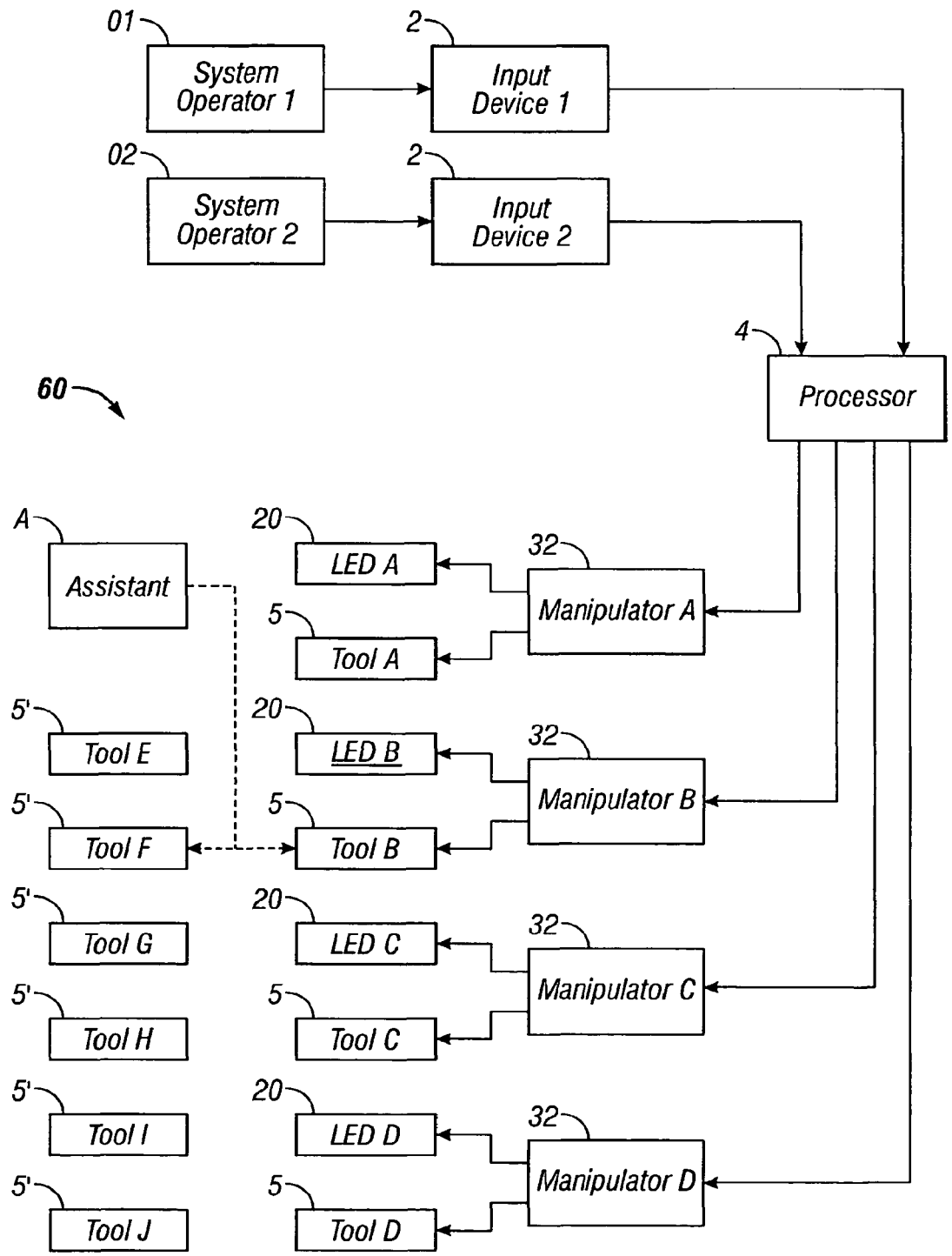
FIG. 8 is a schematic block diagram of an embodiment of an alternative robotic system and method for its use by a plurality of system operators.

Referring now to FIG. 8, a schematic block diagram of a somewhat more complex system 60 is provided. Exemplary cooperative telesurgical systems which may be modified to take advantage of the additional user interface provided by indicators 20 is described in more detail in U.S. Pat. No. 6,659,939, the full disclosure of which is incorporated herein by reference. In the exemplary system of FIG. 8, a first system operator O1 provides input to a first input device 2. Processor 4 selectively couples the movement commands from the first input device 2 to any of a plurality of manipulator assemblies, for example, to manipulator A and manipulator D. A second system operator O2 inputs movement commands to a second input device 2 so as to effect movement of a manipulator 32 manipulator assembly B.

When the second system operator O2 desires the tool 5 attached to manipulator assembly B be replaced an alternate tool 5', for example, tool F, the system operator may verbally instruct assistant A to mount tool F to his manipulator assembly. The indicator 20 of manipulator assembly B generates a signal in response to an appropriate input by the second system operator O2, clearly indicating to the assistant A which tool from which manipulator assembly is to be replaced.

As noted above, additional indicators may optionally be associated with each of the alternative tools 5', thereby foregoing any need for verbal instruction to the assistant regarding which alternative tool is to be mounted to the manipulator. Toward that end, alternative tools 5' may be included in a tool rack 62 which is coupled to processor 4, often so as to provide communication between the circuitry of alternative tools 5' and the processor. This can allow the processor to read identifying information from the tools, thereby allowing the processor to determine which alternative tools or tool types are available and/or appropriate to mount on the manipulator system. An LED or other indicator may be associated with each alternative tool 5' included in the tool rack, and processor 4 may transmit a signal to the tool rack so as to energize one or more indicator associated with one or more tools. Hence, when system operator O1 indicates to processor 4 a desire to replace a mounted tool 5 (for example, tool B on manipulator B) with a different type of tool, a list of available tools and/or tool types may be displayed to the system operator. In response to the system operator selecting (for example, a tool type corresponding to tool F, indicators 20 associated with tool B and tool F may be activated, indicating to the assistant A that these two tools should be exchanged.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 8, the processor may comprise a number of data processing circuits, with at least a portion of the processing optionally being performed adjacent input device 1, a portion being performed adjacent manipulator B, and the like. Any of a wide variety of centralized or distributed data processing architectures may be employed. Similarly, the programming code may be implemented as a number of separate programs or subroutines, or may be integrated into a number of other aspects of the robotic systems described herein.

Figure 9:
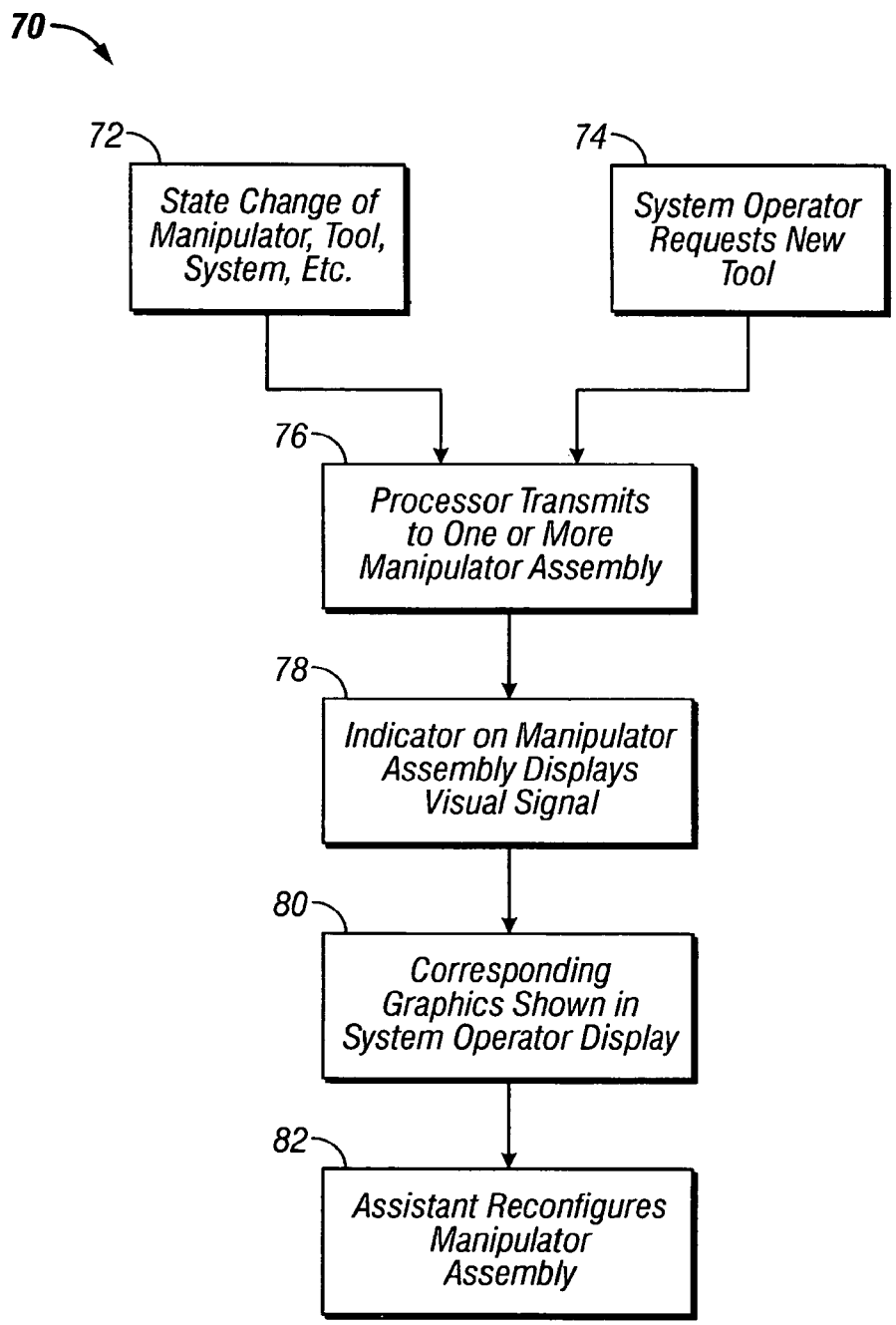
FIG. 9 is a flow chart schematically describing a method for reconfiguring a manipulator assembly in response to an identifiable signal from an associated indicator.

Referring now to FIG. 9, a flowchart 70 schematically illustrates a method for implementing an embodiment of the present invention. The method 70 may begin with a change 72 in state of the manipulator, tool, system, or the like. For example, an assistant may actuate a clutch mode button on the manipulator, the tool may reach the end of its useful life, a manipulator fault may be detected, or the like. In other embodiments, the system operator may initiate method 70 by requesting a new tool 74, or in some other manner indicating which of one or more manipulator assemblies is to generate a signal to be perceived by an assistant or some other person.

Regardless of whether the signal is initiated by a change in state or a system operator, the processor will typically transmit an appropriate command to one or more of the manipulator assemblies 76, and, in response, the indicator on that manipulator assembly will display a visual signal 78. Optionally, corresponding graphics may be shown in a system operator display 80, thereby allowing the system operator to maintain his or her concentration on the internal surgical site.

In response to the visual signal, the other person, such as an assistant, may optionally reconfigure the manipulator assembly 82. For example, the assistant may remove and replace a tool (with its end effector) or may manually reposition the manipulator linkage so as to move the end effector into a desired position. In some embodiments, the assistant may merely monitor the manipulator assembly in response to one or more visual signals, and may optionally prepare to take some appropriate action if the visual signal changes so as to indicate that such an action is appropriate.

FIGS. 10-14 indicate meanings of different signals which may be generated by the exemplary multicolor LED indicators described herein. FIG. 10 shows a potential lexicography for using the indicators as a manipulator user interface ("UI"), while FIG. 11 illustrates some general meanings of signal colors from the indicators. FIG. 12 shows alternative general meanings of the two three-color LED indicators 20 included in each manipulator assembly. By transmitting these or other color signals with sufficient brightness through a clear or translucent plastic cap at a position on the manipulator assembly along the tool insertion axis away from the patient, the signals may be readily identified throughout a wide area. As the red, green, and blue elements of each LED array have a brightness that can be independently controlled, and as the two LED arrays of an indicator may be independently controlled, a wide variety of identifiable signal colors may be generated.

FIG. 13 specifically identifies system, manipulator assembly, and/or tool states that may be associated with several specific signals from the manipulator assembly indicators. Synchronous blinking encompasses blinking of both LED arrays within a single indicator of a manipulator assembly, as can be understood with reference to FIGS. 6 and 7. Alternate blinking encompasses energizing of the two LED arrays with out-of-phase blinking, so that when one LED array is on, the other is off. Still further additional signals may be generated by the indicators to communicate alternative information. For example, signals (such as a quick green blink) may indicate that a component (such as a cannula, sterile adapter, tool or surgical instrument, or the like) that has recently or just been mounted to the manipulator system is valid and accepted. Alternative signals may indicate that a tool change is requested by the system operator, that an energizable instrument (such as an electrocautery instrument or the like) is being activated by the system operator, and the like. Different signal characteristics may optionally be associated with recoverable faults and unrecoverable faults. Hence, a wide variety of still further alternative signals may be included.

While described in some detail, for clarity of understanding and by way of example, a variety of changes, adaptations, and modifications will be obvious to those of skill in the art. Hence, the scope of the present invention is limited solely by the appended claims.

What is claimed is:

1. A medical system comprising:
a master controller;
a manipulator adapted to hold and manipulate each one of a first plurality of medical devices, the first plurality of medical devices including a first medical device mounted on the manipulator and a plurality of unmounted medical devices, the plurality of unmounted medical devices including a replacement medical device;
at least one activatable indicator corresponding to the manipulator;
a plurality of activatable indicators, each of the plurality of activatable indicators corresponding to one of the plurality of unmounted medical devices; and
at least one processor programmed to:
control movement of the manipulator in response to manipulation of the master controller,
control activation of the at least one activatable indicator so as to communicate information that the first medical device should be replaced by the replacement medical device, so that the replacement medical device is mounted on the manipulator, and
control activation of the plurality of activatable indicators so as to indicate the replacement medical device by activating the activatable indicator corresponding to the replacement medical device.

2. The medical system of claim 1, further comprising:
a structure upon which the plurality of unmounted medical devices are each individually and removably placed, wherein each of the plurality of activatable indicators is visually associated with a corresponding one of the plurality of unmounted medical devices.

3. The medical system of claim 1, further comprising:
a second master controller;
a second manipulator adapted to hold and manipulate one of the plurality of unmounted medical devices;
at least one second activatable indicator corresponding to the second manipulator; and
a monitor;
wherein the at least one processor is programmed to:
cause selectable indicators of the manipulator, the second manipulator, and the plurality of unmounted medical devices to be displayed on the monitor;
receive a selection of one of the selectable indicators of the manipulator and the second manipulator, and in response, activate at least one activatable indicator corresponding to the selection of the one of the manipulator and the second manipulator, and
receive a selection of one of the selectable indicators of the plurality of unmounted medical devices, and in response, activate the activatable indicator corresponding to the selection of the one of the plurality of unmounted medical devices.

4. A medical system comprising:
a master controller;
a manipulator adapted to hold and manipulate a medical device;
at least one activatable indicator corresponding to the manipulator;
a second master controller;
a second manipulator adapted to hold and manipulate a second medical device;
at least one second activatable indicator corresponding to the second manipulator; and
at least one processor programmed to:
control movement of the manipulator in response to manipulation of the master controller,
control activation of the at least one activatable indicator so as to communicate an indication that the medical device being held by the manipulator should be replaced by a replacement medical device,
control movement of the second manipulator in response to manipulation of the second master controller, and
control activation of the at least one second activatable indicator so as to communicate an indication that the second medical device being held by the second manipulator should be replaced by a second replacement medical device.

5. The medical system of claim 4, wherein the at least one processor is programmed to activate the at least one activatable indicator if a first replacement command associated with the master controller is received, and to activate the at least one second activatable indicator if a second replacement command associated with the second master controller is received.

6. A medical system comprising:

a master controller;

a manipulator adapted to hold and manipulate a medical device;

at least one activatable indicator corresponding to the manipulator;

a monitor; and at least one processor programmed to:

control movement of the manipulator in response to manipulation of the master controller, control activation of the at least one activatable indicator so as to communicate information that the medical device being held by the manipulator should be replaced by a replacement medical device, receive information that identifies each one of a plurality of unmounted medical devices, generate a list of available medical devices by using the received information that identifies each one of the plurality of unmounted medical devices, and display the list of available medical devices on the monitor.

7. The medical system of claim 6, further comprising:

a plurality of activatable indicators, each of the plurality of activatable indicators corresponding to one of the plurality of unmounted medical devices;

wherein the at least one processor is programmed to respond to a selection of the replacement medical device from the list of available medical devices by activating a corresponding one of the plurality of activatable indicators.

* * * * *